(12) United States Patent
Vrane et al.

(10) Patent No.: US 6,767,188 B2
(45) Date of Patent: Jul. 27, 2004

(54) CONSTANT OUTPUT FLUIDIC SYSTEM

(75) Inventors: David R. Vrane, San Jose, CA (US); Pierce Norton, Morgan Hill, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 64 days.

(21) Appl. No.: 10/222,639

(22) Filed: Aug. 15, 2002

(65) Prior Publication Data

US 2004/0031521 A1 Feb. 19, 2004

(51) Int. Cl.[7] .................................................. G05D 7/00
(52) U.S. Cl. ........................ 417/40; 137/207; 137/208
(58) Field of Search ................................ 137/207, 208; 417/40

(56) References Cited

U.S. PATENT DOCUMENTS

| | | | |
|---|---|---|---|
| 5,915,925 A | 6/1999 | North, Jr. | ...................... 417/36 |
| 5,971,713 A | 10/1999 | North, Jr. | ...................... 417/36 |
| 6,017,194 A | 1/2000 | North, Jr. | ...................... 417/36 |
| 6,200,101 B1 | 3/2001 | North, Jr. | ...................... 417/36 |
| 6,227,807 B1 | 5/2001 | Chase | ........................ 417/44.1 |

*Primary Examiner*—Gerald A. Michalsky
(74) *Attorney, Agent, or Firm*—Douglas A. Perry

(57) ABSTRACT

A device for conditioning of fluid to minimize pulses from a pump source. A pump drives fluid from a vented fluid reservoir through a system including a combination of an attenuation tank and one or more orifice. Fluid is pumped into a plenum chamber that supplies fluid in a pulse free flow stream. A pressurized head over the fluid in the plenum chamber allows fluid delivery at a selected pressure. A volume sensor monitors the fluid level within the plenum tank and activates the pump if fluid level falls below a specified level.

21 Claims, 6 Drawing Sheets

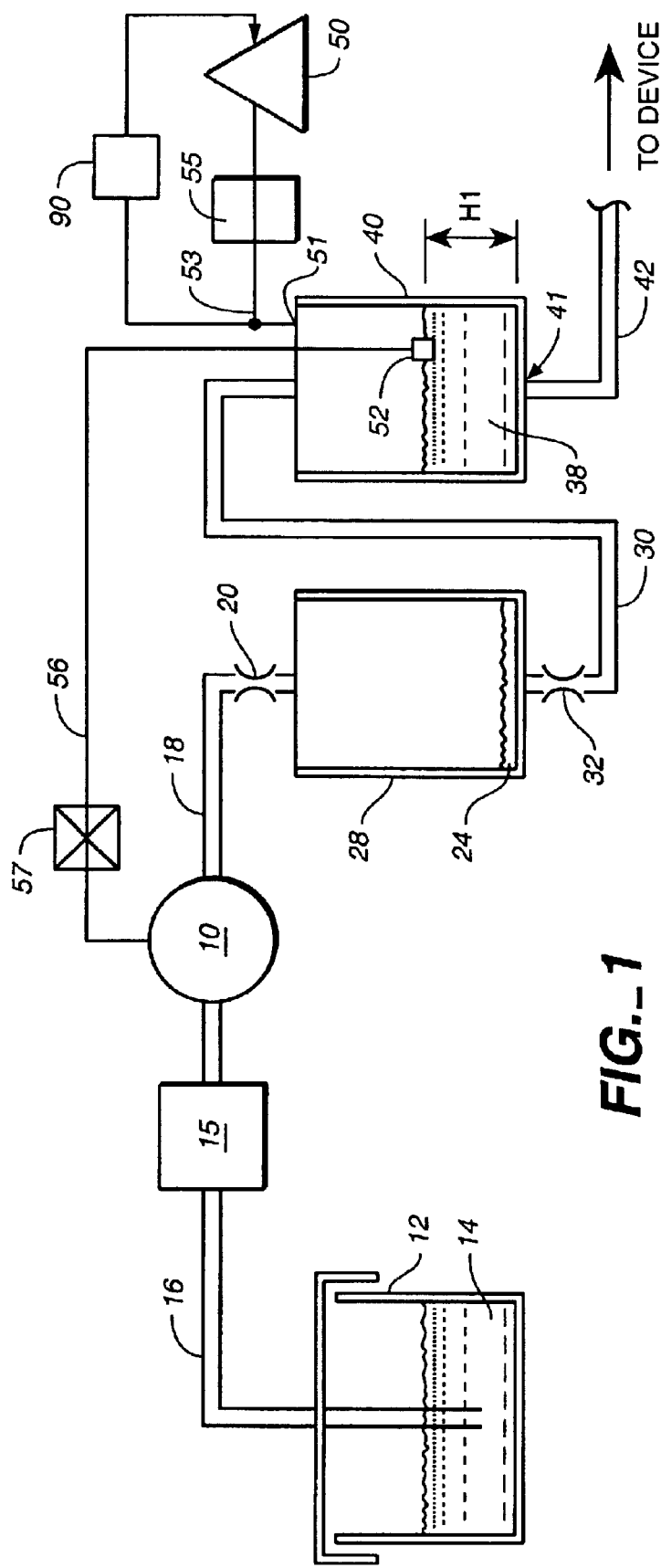
FIG._1

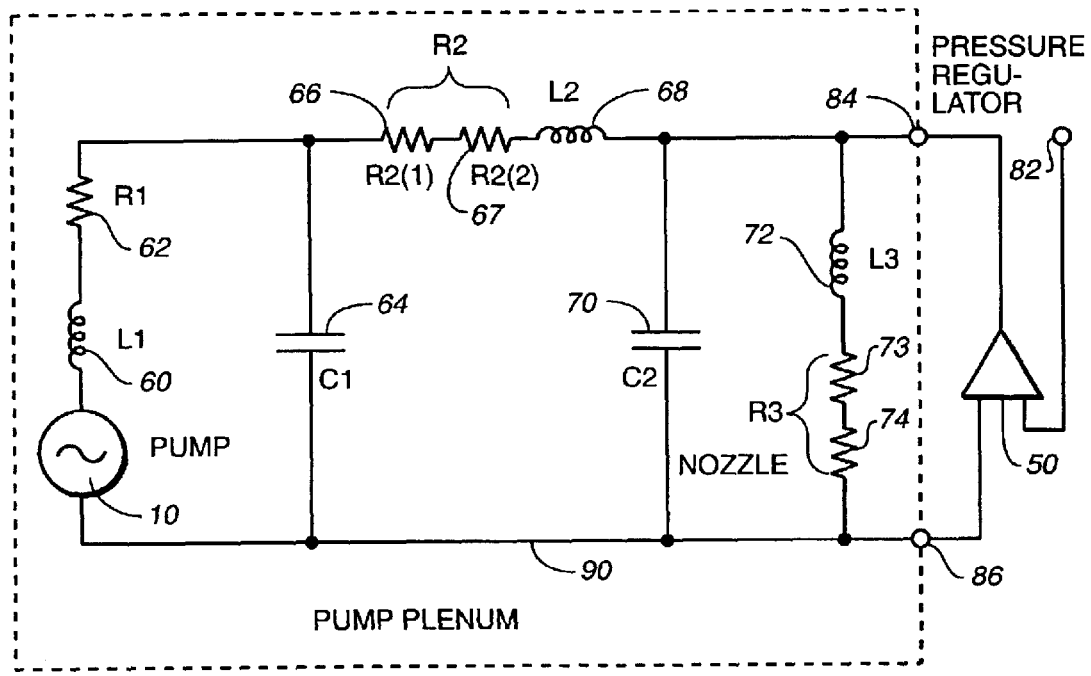
FIG._2
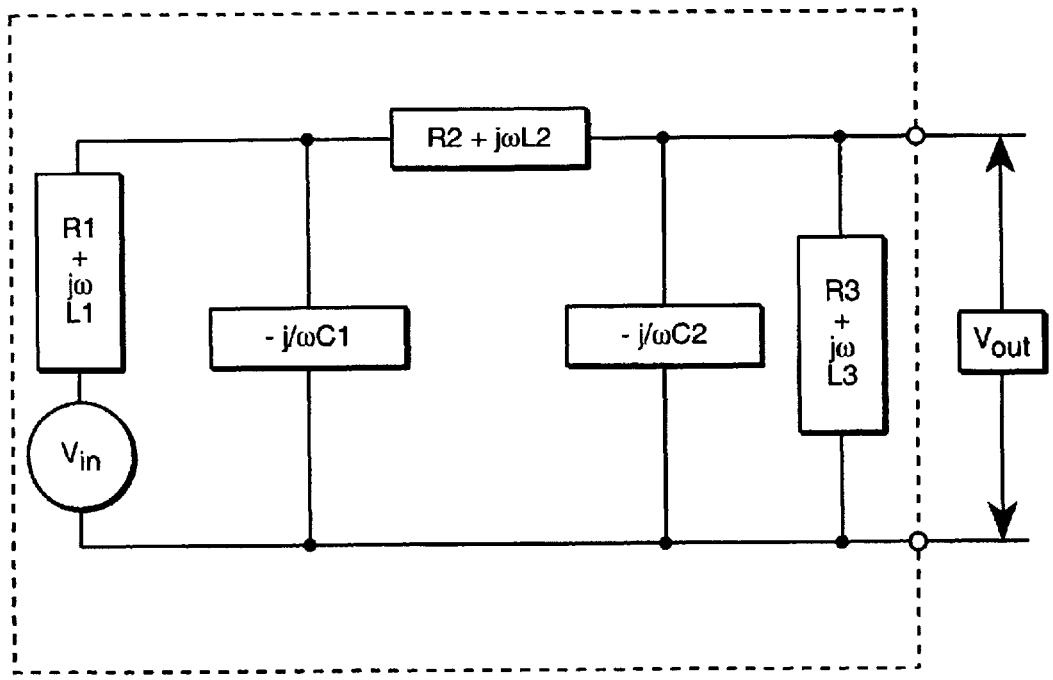
FIG._3

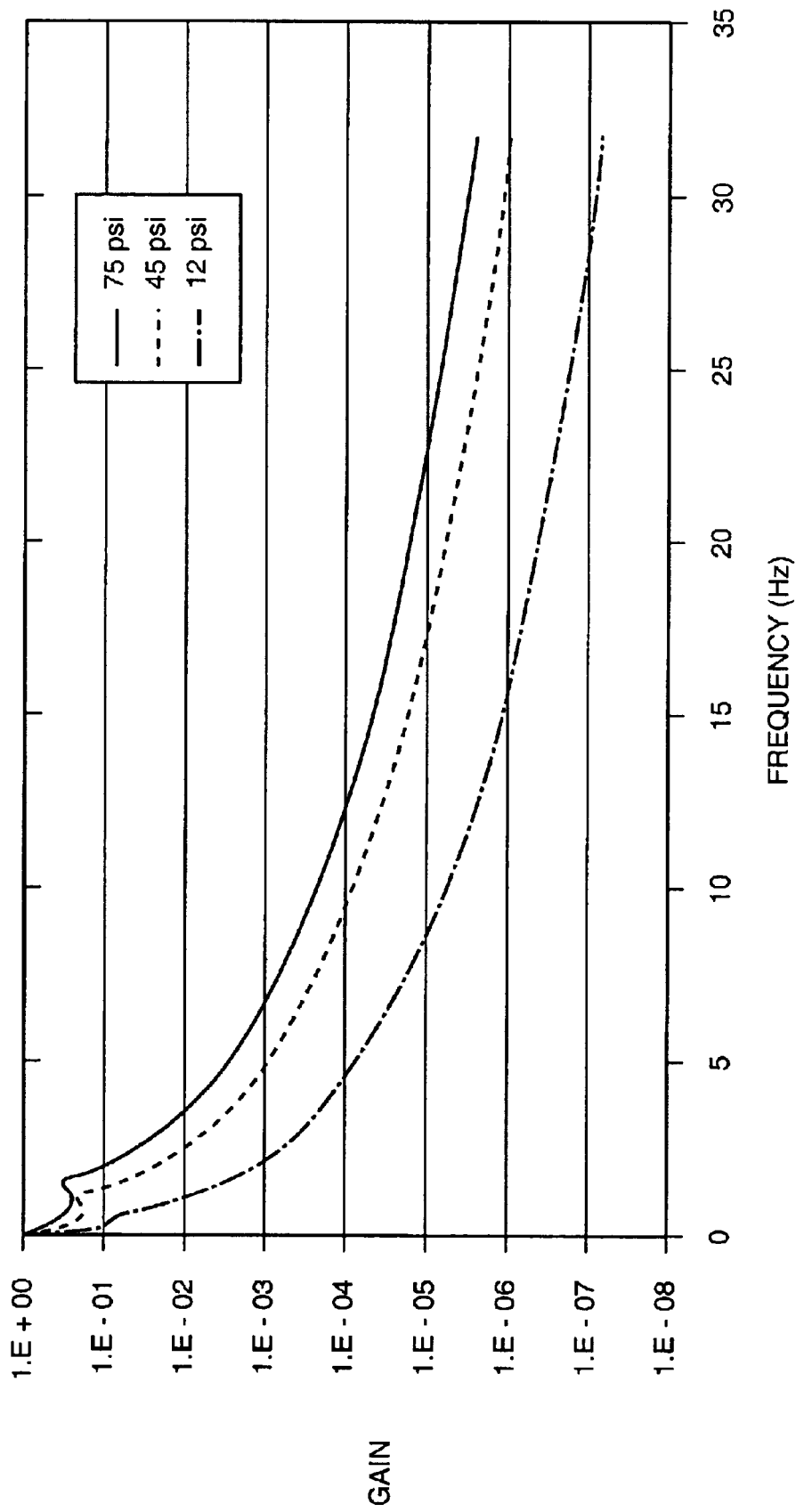
FIG._4

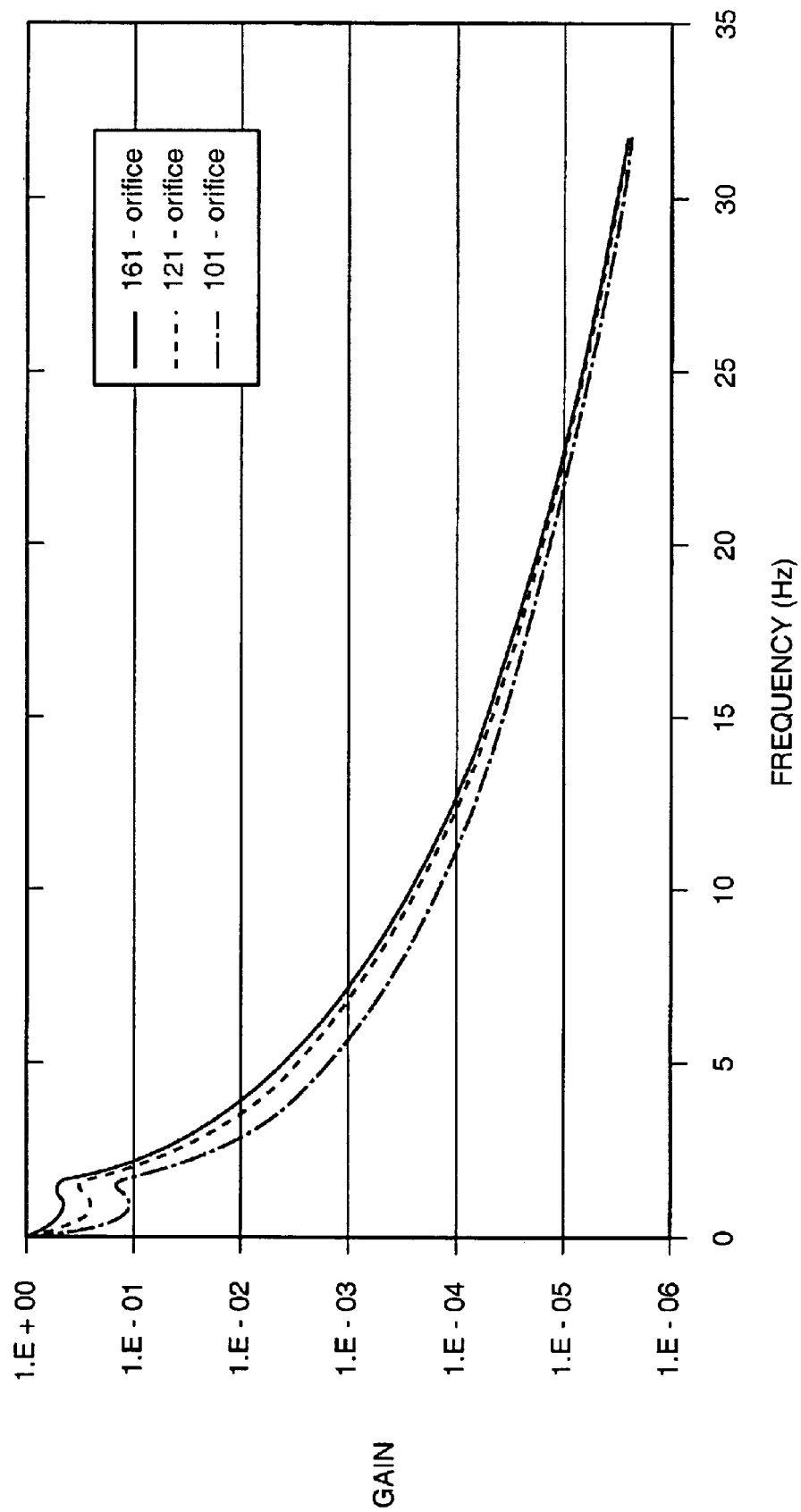
FIG._5

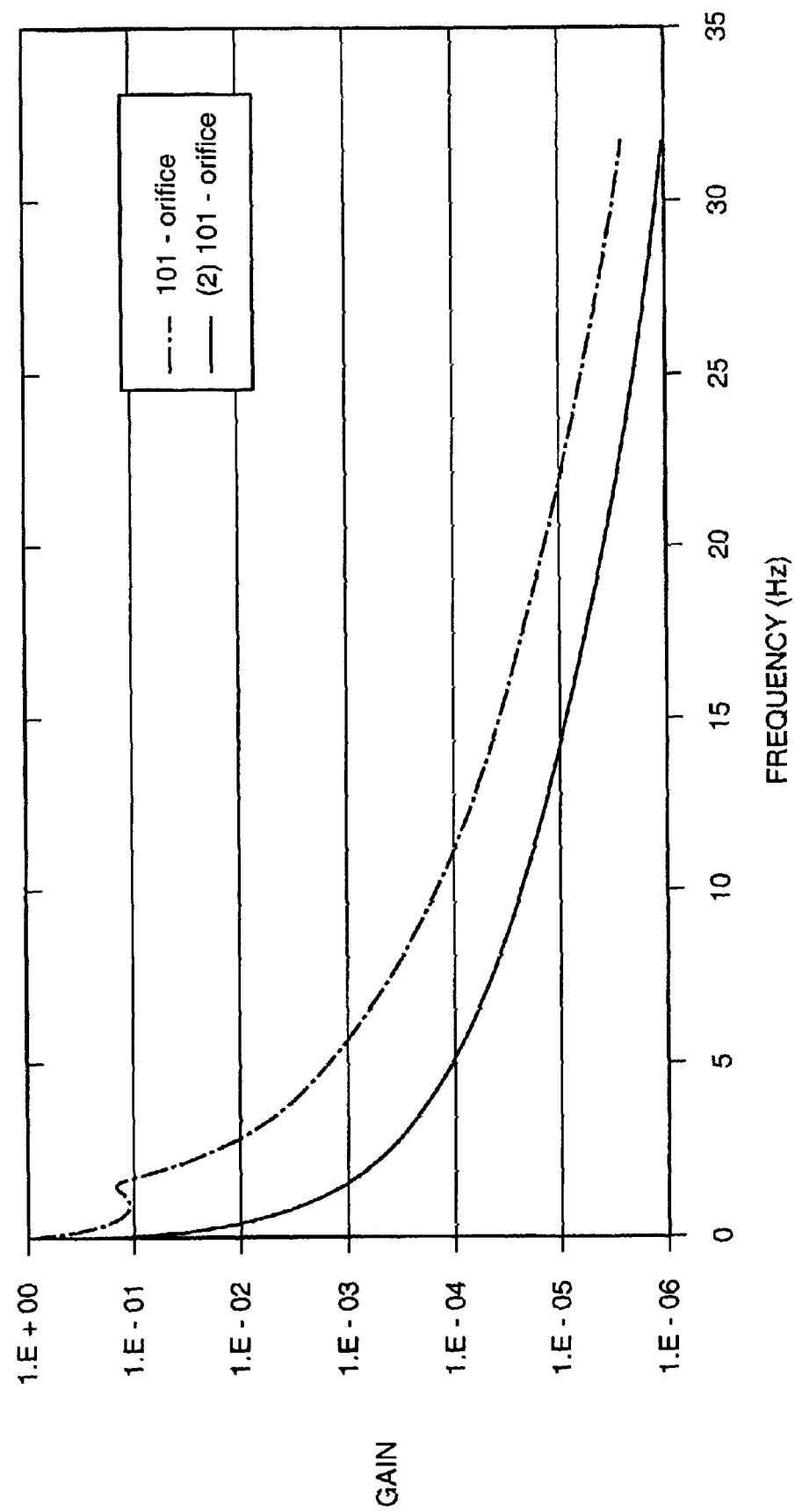
FIG._6

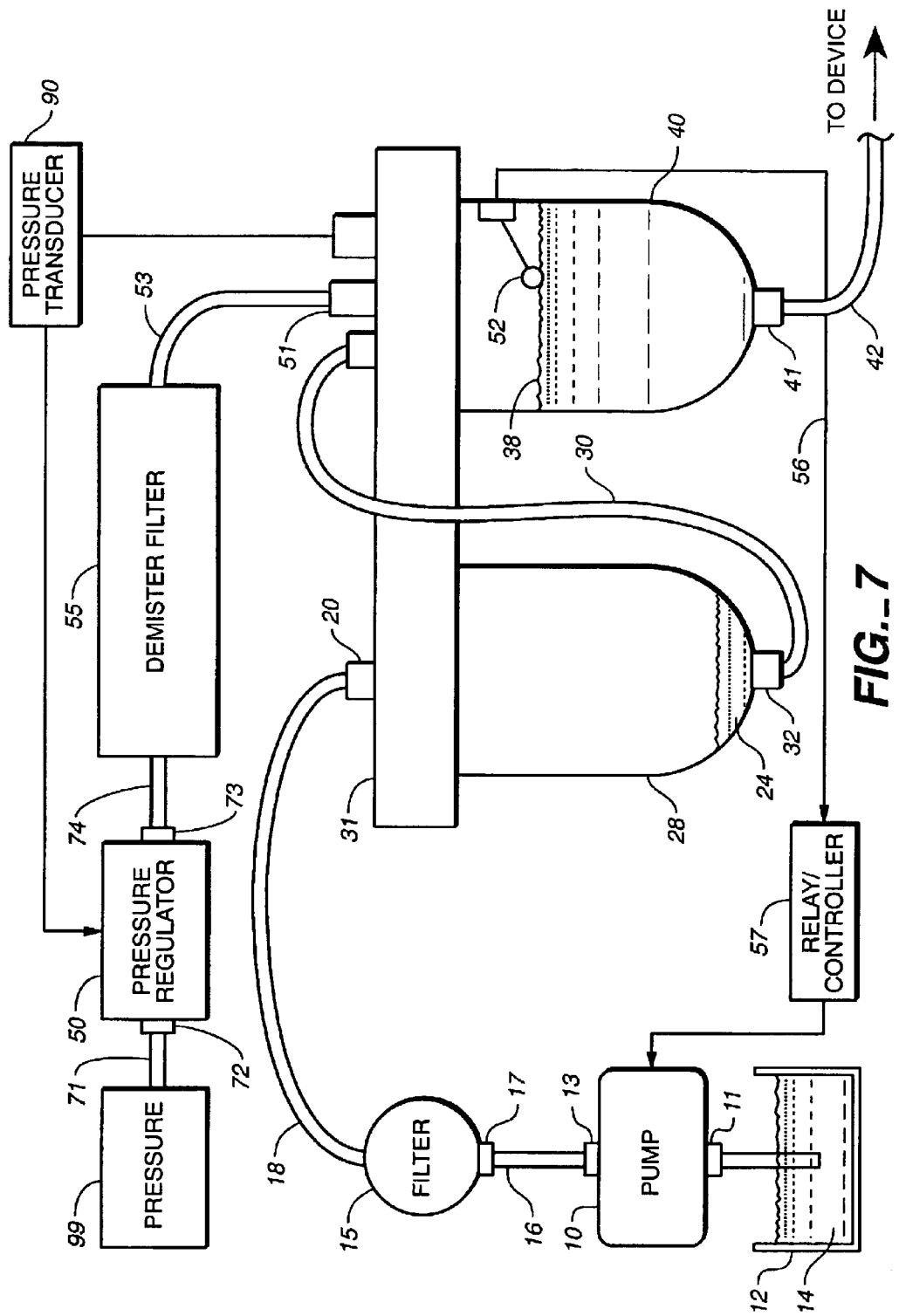
FIG._7

CONSTANT OUTPUT FLUIDIC SYSTEM

TECHNICAL FIELD

The present invention relates to a system for regulation of fluid flow and more specifically to a system that can pump liquid from a vented container and deliver the liquid at a pulse free flow to an instrument.

BACKGROUND OF THE INVENTION

Flow analysis has been used in research and clinical applications to analyze the characteristics of particulate targets. In this system a particle stream is injected into the center of a sheath flow stream. The resulting laminar flow is passed through an optical detection location, where the stream is illuminated and fluorescence and/or light scatter is measured from passing target particles. In sorting analyzers, the flow stream may subsequently divided into droplets, with targeted particles separated into droplets. These droplets could then be sorted to recover the particle of interest.

The requirements of a robust sheath flow delivery system are a) that it provides an adequate flow capacity and b) that it present a negligibly small temporal flow variation. The flow variation is especially important for sorting application. During a sorting operation a target is analyzed and identified at a first location, droplets are generated downstream at a second location, droplets are tagged for sorting at a third downstream location (generally by applying a charge to the droplet), and droplets are sorted at a fourth downstream location (e.g. by passing charged droplets between charged plates). The first through fourth locations are separated along a flow path. Sorting of droplets requires precise correspondence between target recognition, droplet generation, and droplet charging and deflection. If fluid velocity varies in pulses, such coordination of events becomes extremely difficult.

The sheath flow liquid used in flow cytometry is generally a phosphate buffered saline or other isotonic solution. In prior flow analysis systems, a pressurized reservoir was used to supply the flow stream. A regulator provides a static air pressure over the free surface of the sheath flow fluid within a large, rigid tank. For high pressure systems this tank would usually be a stainless steel pressurized tank. For lower pressure applications the tank would be made of reinforced plastic. The pressure in the tank drives the fluid in the tank to an outlet tube leading to the flow analysis cell.

In such large tank systems the pressure head over sheath flow liquid within a tank is varied to compensate for pressure loss as fluid level in the tank decreases. Because the flow volume requirement of the cytometer is small compared to the volume within the tank, the pressure variation associated with volume change is gradual. It is fairly easy for a pressure regulator to vary the pressure within the tank to compensate for the pressure change caused by the declining fluid level within the tank.

There are a number of drawbacks to this system. First, the system is bulky and expensive. Second, this system is relatively difficult to use. Manipulation of the large, heavy sheath flow tanks is cumbersome. Third, the system lacks flexibility. To add or exchange the sheath flow fluid the tank must be depressurized, supply lines disconnected, the tank refilled (or emptied and refilled) and repressurized. This results in system down time and requires some expertise to insure consistency in system performance. In many present systems, the pressure regulator does not automatically compensate for pressure variation associated with changes in the tank fluid level. Instead the operator must adjust the regulator pressure periodically as the level in the sheath tank changes. This requires operator time and could result in error.

Different solutions providing a method to generate a pulse free pumping from a vented container have been proposed. U.S. Pat. No. 6,227,807 discloses a means for controlling the output flow of a pump. The radial speed of the pump is controlled during discreet segments of the motor's radial path during pump revolutions. This is performed by a memory, counter and amplifier. These control the speed of the pump stepper motor at discrete points in the pump cycle. The down stroke time is minimized and a flow interruption filter suppresses the interruption of the flow during the upstroke.

U.S. Pat. Nos. 6,017,194 and 6,200,101 disclose a method and apparatus for providing consistent liquid pressure output. In this device, liquid is pumped from a vented container by a pump into a liquid accumulator. A volume sensor of fluid within the accumulator is used to control the pump such that liquid within the accumulator is maintained at a constant height. The negative spring rate of the accumulator piston is equal to the sum of the positive spring rates of the accumulator control spring, diaphragm piston, and flexure support sensor lever. The flexure support sensor lever moves the accumulator diaphragm, which triggers a signal to the pump. This feedback loop regulates pump speed to maintain a constant level of liquid within a liquid accumulator.

While these solutions allow for pumping from a vented container, alternative methods of producing a uniform pump flow would be desirable.

It is an object of the invention to provide a flow system that provides a constant flow. This system should be supplied from a user selected, nonpressurized container. It should not be affected by the level of fluid level in this nonpressurized container.

It is a further object to provide such a system having lower material requirements. Such a system would have a lower weight and a smaller bench space requirement.

It is a further object of the invention to provide a system that requires less precise pump control and is adaptable for use with available pulsile pumps.

These objects have been achieved through a sheath supply system that uses a pump to draw liquid from a non-pressurized container and pump this liquid into a supply line which empties into an attenuation chamber. Liquid flows from an outlet in the attenuation chamber to the plenum chamber through a tube. At least one orifice restricts the diameter of flow between the pump and the plenum chamber. The combination of the attenuation chamber and the orifice act as a first shock wave dampener for pump pulses.

Liquid flows through the orifice into a plenum chamber. Liquid within this chamber is maintained at a specific height within the chamber. A pressure transducer regulates the pressure head over this liquid. The height of liquid within the chamber, as determined by a sensor, is regulated by turning the pump on and off. This plenum chamber acts as a second wave shock absorber, further attenuating pulses in fluid flow. At the bottom of the plenum chamber is an outlet, which leads to an analytical system such as a flow cytometer, blood analyzer, or other device requiring a constant fluid flow at a constant pressure and conditioned to substantially pulse free.

BRIEF DESCRIPTION OF THE DRAWINGS

FIG. 1 is a schematic of one fluid regulation system.

FIG. 2 is a schematic of a model of the system.

FIG. 3 is the complex phasor form of the model of FIG. 2.

FIG. 4 shows a graph of sheath pulse attenuation for pump operating at different frequencies.

FIG. 5 is a graph of sheath flow pulse attenuation for orifices of different sizes at different pump frequencies.

FIG. 6 is a graph of sheath flow pulse attenuation at different frequencies for a system including a single and two tandem orifices.

FIG. 7 is a view of one implementation of the present invention.

DESCRIPTION OF THE INVENTION

The present system allows liquid to be pumped from an unpressurized supply container and supply this liquid free from both pump pulsations or pressure variation due to changing liquid level in the supply container. The liquid is supplied to an analytical apparatus at a selectable pressure.

The pulsating nature of the pump flow prevents flow directly from the pump from being suitable for use with a flow cytometer without first conditioning the flow to attenuate the pulsation. Without attenuation, the pulsation in the liquid would adversely affect the performance of the flow cytometer or other analytical device to which the flow is directed.

The output of the pump is affected by the amount of liquid within the supply container. The changing pressure within a supply container (as the liquid level within the container changes as fluid is withdrawn) will affect the pulsations of the pump. The use of two pulse dampeners acts to attenuate the pulsation of the pump sufficiently so that the pulsation does not affect the performance of the analytical system.

System Implementation

With reference to FIG. 1, the schematic shows pulsile pump 10 having an inlet tube 16 placed in sheath flow liquid 14 in vented supply container 12. This pump could be a positive displacement pump that supplies fluid in a pulsing flow. Container 12 is not pressurized and can be refilled while the pump is running and the pressurized fluid is flowing out of this system. Pump 10 pumps fluid from supply container 12, through filter 15 into pump line 18. The liquid is pumped through orifice 20 into attenuation chamber 28. Sheath fluid 14 flows from attenuation chamber 28 through orifice 32 at the attenuation chamber outflow. As liquid is pumped into attenuation chamber 28 through orifice 20 liquid will be forced out of attenuation chamber 28 through orifice 32.

Fluid flows through orifice 32 into tube 30. Fluid moves through tube 30, into plenum chamber 40. Attenuation chamber 28 in combination with orifice 20 act as a first pulse wave dampener and dissipate much of the flow pulse from pump 10. Plenum chamber 40 and orifice 32 acts as a second pulse wave dampener to further attenuate the pulse from pump 10.

The sheath flow fluid 38 within plenum chamber 40 is held at a height H1 that is within a defined range. When fluid level of sheath flow fluid 38, as determined by float sensor 52, begins to fall, a signal is sent through connection 56 to pump 10. The pump is activated and additional fluid is pumped into tube 18. When the fluid level within plenum chamber 40 has reached sufficient height, a signal is sent through connection 56 to deactivate the pump. Float sensor 52 and connector 56 may include an electronic controller 57, which receives a signal from float sensor 52 and transfers this signal to pump 10.

The pressure head over fluid within plenum chamber 40 is controlled by pressure regulator 50. Pressure regulator introduces pressure into plenum chamber 40 through inlet 51. Pressurized gas is introduced into plenum chamber 40 through tube 53 from pressure regulator 50. Pressurized gas moves through filter/demister 55 before entering plenum chamber 40. The pressure head over fluid within plenum chamber 40 is held constant. Applied pressure over the liquid free surface drives the fluid from the plenum chamber through an exit port 41 into a tube 42 leading to the analytical device. This system thus allows fluid to be drawn from a vented or non-pressurized container and supplies this liquid, free from both pump pulsation and pressure variations due to changing levels of fluid within the supply container, to a flow cytometer or other analytical device at a specified pressure. The supply tank may even be exchanged while the plenum chamber is supplying a flow of sheath fluid to the system. This would occur without disturbing the flow as long as the liquid level within the plenum were within the set height tolerances.

Model of the System

A model of the system has been developed to provide a better understanding of the present system. This model predicts performance and may be adapted to the variation in components used with the system. Thus, if the specifications of the pump are known, the model can use this information to determine the requirements of the other elements (e.g. chamber dimensions, orifice dimensions, etc.).

In this model the use of a single orifice is considered. The illustration of this model is shown in FIG. 2. The pump, 10, is modeled as an AC power supply. The inductor 60 and the first resistor 62 are properties of the tubing from the pump to the attenuation chamber. The attenuation chamber is modeled as capacitor 64. The orifice is modeled as resistor 66 and the tubing of connecting the attenuation chamber and plenum chamber is modeled as inductor 68 and resistor 67. The plenum chamber is modeled as capacitor 70. The pipe leaving plenum chamber acts as inductor 72, and resistor 73 and the nozzle from which the fluid flows in the flow cell is resistor 74. The pressure regulator 50 is connected by nodes 84, 86 into the system. The pressure transducer 90 feedback control is indicated as as node 82. Using this model the fluid attenuation may be analyzed. The elements outside the dotted line are not integral to the model analysis.

The model of electrical circuitry may be adapted to fluidic systems. The present sheath fluid system modeled as an analog electrical circuit is shown in FIG. 2. In FIG. 2 the symbols R, L and C represent the resistance, inductance and capacitance of the fluid element of the system, respectively. The resistance would be resistance to flow, the inductance would represent flow momentum and capacitance is a measure of the change in pressure as a function of volume within a container. The electrical and fluidic model is such that electrical principles may be analogized to the fluid operations. The values of each element (resistance, inductance, and capacitance) depend on the physical properties of the fluid (e.g. viscosity) as well as the physical dimensions of the individual fluidic elements.

Resistance can arise from either viscous drag or convective acceleration. The relation between pressure drop, volumetric flow rate and viscous resistance of fully developed flow passing through a pipe is analogous to Ohm's law:

$$V=IR:P=QR$$

Where Voltage V is analogous to Pressure P, current I is analogous to flow rate Q, and electrical resistance R is analogous to fluid resistance R.

The viscous resistance of fully developed flow passing through a circular cross sectional pipe is given by:

$$R = \frac{128\,\mu L}{\pi d^4}$$

Where $\mu$ is the dynamic viscosity of the fluid, L is the pipe length (of a circular cross sectional pipe), and d is the diameter of the pipe. In the case of convective acceleration, flow resistance results from a sudden change in fluid momentum. Applying this model to a fluidic element, for an orifice the pressure drop from one side of the orifice to the other is proportional to the square of the velocity of the stream.

However, for small fluctuations about a mean velocity (as with fluidic pulses), the relationship between the orifice and velocity is linearized to facilitate frequency analysis. In the current model, the linearized resistance values for the orifice and nozzle are derived from manufacturer data and empirical measurements of velocity.

Inductance arises from local acceleration of fluid mass that is passing through a particular fluidic element (such as an pipe). The relation for fluid inductance through a passage of length L and area A is analogized from Newton's second law:

$$F = ma : P = \frac{\rho L}{A}\frac{DQ}{Dt}$$

Where F is force, m is the mass, a is acceleration and $\rho$ is the density of the fluid. The relation on the right side of the colon is analogous to the Faraday/Henry relation for electrical inductance:

$$v = L\frac{DI}{Dt} : P = \frac{\rho L}{A}\frac{DQ}{Dt}$$

From this relation it follows that the inductance (L) of a circular pipe of length L and diameter d is given by:

$$L = \frac{4\rho L}{\pi d^2}$$

Capacitance in a fluidic circuit can arise from two main sources: (1) deformation (or compliance) of solid containment walls or tubing; and (2) compressibility of a fluid phase. In the case where liquid water is the only phase, the main source of capacitance usually comes from (1). However, where a compressible gas at relatively low pressures is also present, type (2) capacitance usually dominates over the effect of container deformation, especially if the container is made of a rigid material. In the present system, the attenuation chamber has a head of compressible gas and the effect of type (2) capacitance will predominate. The expression for type (2) capacitance is derived directly from Conservation of Mass and the Ideal Gas Law. The result is analogous to the Maxwell relation for electrical capacitance:

$$I = C\frac{DV}{Dt} : Q = \frac{v}{P}\frac{DP}{Dt}$$

Where ratio of gas volume, v, to the mean pressure, P, is the fluid capacitance, C. For small enough variations in the pressure this ratio is considered constant, allowing linear treatment of the system. For a cylindrical air volume of height, H, and diameter, D, the fluid capacitance is expressed as:

$$C = \frac{H\pi D^2}{4P}$$

With the fluidic elements defined in terms of physical parameters, the circuit of FIG. 1 is converted to phasor form as shown below [Hayt et al., 1986]. The goal of this circuit is to produce a constant voltage output given input with both DC and AC components. Given the linearity of the circuit we need only consider (and minimize) the gain on the time dependent portion of the input signal. To do this, the circuit shown in FIG. 2 is recast in the complex phasor, frequency domain form, shown in FIG. 3. Here, w is frequency (given in radians/second). In phasor form, the complex impedances, shown in FIG. 3, are manipulated through the use of Kirchoff's current and voltage laws to produce the following transform function for the system gain:

$$\frac{V_{out}}{V_{in}} = \frac{Z_2 Z_4}{Z_1 Z_2 + (Z_1 + Z_2)(Z_3 + Z_4)}$$

Where, $$Z_z = R1 + j\omega L1$$

$$Z_2 = \frac{1}{j\omega C1}$$

$$Z_3 = R2 + j\omega L2$$

$$Z_4 = \frac{R3 + j\omega L3}{1 - \omega^2 C2 L3 + j\omega C2 R3}$$

Analytical Application of the Model

Physical values for impedance were calculated based upon the rough dimensions of a sheath supply breadboard. These values are given in Table 1 for a system pressure of 75-psi. While not shown here, operating pressures of 45-psi and 12-psi were also considered. The orifice resistance was based upon the pump flow rate of approximately 80 ml/min, operating at a 7% duty cycle. The working fluids of the model were water and air (water has a viscosity sufficiently similar to the viscosity of the buffered saline solutions commonly used as sheath flow that this is sufficient for the present model). The density and dynamic viscosity of water at 20° C. were taken to be 998-kg/m3 and 10.03E−4-Pa*s.

FIG. 4 shows the pulse-filtering performance of the plenum sheath supply as a function of the operating pressure. The presence of the pole is a characteristic a second order system. At 75 psi, this pole, or resonance point, occurs at approximately 1.65-Hz. At lower pressures, viscous resistance and increased air compressibility attenuate the pole's gain and resonant frequency. This results in improved attenuation performance at lower pressures for a given pumping frequency.

At the current pumping frequency of 4.36-Hz, the gain at 75-psi is approximately 4.96E−3. This system, as shown in table 1, uses an Air Logic, San Jose, Calif. 0.012 inch diameter orifice restriction between the attenuation and plenum chambers. However, mild improvements in attenuation can be obtained through smaller orifice selection. FIG. 5 shows the influence of orifice size on attenuation performance. By changing the orifice from 0.012 inch diameter to 0.010 inch diameter attenuation drops to 2.35E−3 at 75-psi. Changes in orifice size have the largest effect at low frequencies while at higher frequencies the gain curves asymptotically collapse onto a single curve, as shown in FIG. 5. However, the poor performance at low frequency generally suggests low frequency pumps (or pump operation) are best avoided.

The attenuation of the system can be improved further by inspection of the $V_{out}$ to $V_{in}$ ratio. Increases in Z1 and Z3 provide direct means of improving attenuation as these terms only appear in the denominator. As Z3 (through R3) is already by far the largest impedance in the system, the easiest improvement in attenuation is achieved by increasing Z1 by increasing the resistance value of 62. FIG. 6 shows the effect of placing a second Air Logic 0.01 inch diameter orifice in the sheath line before the attenuation tank. As a result of the additional orifice, the gain drops from 2.35E–3 to 1.42E–4, at 4.36-Hz, to give a pulse attenuation of 0.014%. A pulse attenuation of better than $1*10^{-3}$ is believed sufficient for flow cytometry performance.

Tube 18 leads to the attenuation chamber 28. The inlet 20 and the outflow 32 of attenuation chamber 28 include orifices. Integral 0.01 inch Air Logic orifices are used in one implementation. The combination of the attenuation chamber and one or more orifices allows for substantial conditioning of the pulses from the pump. Liquid flows from orifice 32 before it reaches the plenum chamber 40, further conditioning the fluid flow. In one implementation all liquid lines are connected to the system using 0.0625"-I.D., 10-32 hose barb fittings.

Fluid flows from the plenum chamber 40 into outlet hose 42 joined to plenum chamber 40 through outlet barb 41. Outlet hose 42 carries the sheath flow liquid to an analytical instrument (not shown).

| Description | Parameter | Units | Value | Diameter | Length |
|---|---|---|---|---|---|
| Voltage/Pressure | V | Pa | 75 | NA | NA |
| Current/Flow-rate | Q | cm^3/min | 6 | NA | NA |
| Sheath line resistance | R1 | Pa*min/cm^3 | 1.539 | .3175/.47625 | 20/15 |
| Orifice line resistance | R2(1) | Pa*min/cm^3 | 32.17 | 0.15875 | 30/30 |
| Orifice resistance (mfg. data) | R2(2) | Pa*min/cm^3 | 73.05 | 0.03048 | NA |
| Flow cell line resistance | R3(1) | Pa*min/cm^3 | 348.7 | 198.12/35.56/91.44 | 0.15875 |
| Flow cell resistance (est.) | R3(2) | Pa*min/cm^3 | 80090.18 | NA | NA |
| Sheath line inductance | L1 | Pa*min^2/cm^3 | 0.5597 | .3175/.47625 | 20/15 |
| Orifice line inductance | L2 | Pa*min^2/cm^3 | 2.519 | 0.15875 | 30/30 |
| Flow cell line inductance | L3 | Pa*min^2/cm^3 | 27.29 | 198.12/35.56/91.44 | 0.15875 |
| Attenuation tank capacitance | C1 | cm^3/Pa | 1.81E–02 | 6.3 | 5 |
| Plenum tank capacitance | C2 | cm^3/Pa | 9.04E–03 | 6.3 | 2.5 |

Table 1 shows physical valves for fluidic elements and their conversion to analog electrical element parameters for a plenum sheath supply system operating at 75-psi with a steady-state volumetric flow rate of 6-ml/min.

SYSTEM EXAMPLE

FIG. 7 illustrates a system designed to implement the model. FIG. 7 shows a stand-alone version of the system, which may be mounted on an analytical system in some implementations.

With reference to FIG. 7, on a back plate is mounted a base plate 31. The back plate is an aluminum mounting plate while base plate 31 is made from PVC. Plenum chamber 40 and attenuation chamber 28 are made of the same material as the base plate 31 and are secured to base plate 31 using buttress threads. O-rings are used to seal the lip of plenum chamber 40 and attenuation chamber 28 to the receiving surface of the base plate. This ensures a secure seal for each chamber and provides leak free performance at 75 psi. Leak free performance at higher psi is expected but was not tested.

In the system the pump 10 withdraws liquid from a nonpressurized container 12 containing sheath flow liquid 14. This liquid is drawn into tube 16 which leads to pump inlet 11 on pump 10. The pump selected for this implementation of the system is a modified-stroke KNF NF1.30 diaphragm pump. Fluid leaves pump 10 through outlet 13 into tube 16 which is joined to inlet 17. Inlet 17 directs fluid though filter 15, to ensure that particulate matter is removed from the fluid prior to the fluid entering the pressure conditioning elements and the analytical device. In one implementation of this device the filter is a Pall Ultipor N66 0.2-um filter. After passing through filter 15 the fluid flows into tube 18.

The system includes an air pressurization system to maintain the pressure within plenum chamber 40 within a set tolerance. Gas intake hose 71 provides an intake of gas into gas intake port 72 on control air pressure 50. Gas (e.g. air) at a controlled pressure is introduced into tube 74 through outflow port 73. The pressurized gas moves though tube 74 and into a filter/demister assembly 55. This insures that the gas evacuating from the plenum chamber upon depressurization does not contain liquid that could damage the regulator or otherwise affect system performance. This system also ensures that no particulate matter is introduced into the plenum chamber. The outflow tube 53 leading from the filter/demister is joined to plenum chamber 40 through coupling 51. Pressure transmitter 90 measures the pressure within plenum chamber 40 and transmits this measurement via an electronic link to the pressure transducer.

In one implementation of this invention, regulated air is supplied to the system using a Control Air type 900EX-pressure regulator. An SMC NAFM/NAF 2000 de-mister/air filter is placed between the pressure regulator and plenum chamber to prevent moisture from damaging the regulator during pressure relief operations. A Tescom 100-100-2127 pressure transducer is used to measure the actual pressure in the plenum chamber.

The system also includes a system to regulate the pump flow by activating or deactivating the pump to maintain the fluid level in plenum chamber 40 at within a height tolerance. Float sensor 52 determines the fluid level within plenum chamber 40. The signal from sensor 52 is transmitted via wire 56. Wire 56 is shown transmitting to a relay 57. The relay 57 is electronically linked to pump 10 such that relay activates pump 10 when the level within the plenum chamber is below a selected level and deactivates pump 10 when the fluid level is above a selected level. This maintains the level of fluid within a set tolerance. In one implementation of the present invention the power to the pump is controlled, via relay, by a GEMS LS-300 float switch to maintain liquid level in the plenum chamber.

A number of alternative arrangement of this exemplary system are contemplated. The system may be a stand alone device or may be incorporated as part of a flow cytometer or other analytical system. If this system is implemented as part of a larger system, all of the elements of the system may be on one side of a breadboard. As a stand alone system the elements can be on one side or both sides of the breadboard. In addition the electronic controls may be tied into the electronics of the rest of the system.

A number of alternatives exist for various elements of the present device. The fluid level sensor, illustrated as a float sensor, could also be an optical sensor or any other device for determining the fluid level within a container. The air pressure regulation also may be any combination of elements which allow the plenum chamber to be maintained at a constant pressure. A number of different materials could be adapted to the present device. The gas in the plenum chamber can be either gas supplied from a tank or be air. The gas and sheath flow liquid prior to intake can be drawn through a pre-filter. Other alternatives are possible for adopting the present system to specific applications.

What is claimed is:

1. A system for providing a constant fluid flow from a reservoir fluid source, the system comprising;
    a pulsile pump that pumps fluid from said reservoir;
    a pulse attenuator in fluid communication with said pump, said attenuator dampening pulses of fluid;
    a plenum chamber receiving liquid from said attenuator;
    a volume sensor which senses fluid volume within said plenum chamber, said sensor activating said pump when said fluid volume within said plenum chamber falls below a specified level and deactivating said pump when said fluid volume within said plenum chamber is above a specified level;
    a pressurization source in fluid communication with said plenum chamber, said pressurization source providing a pressure head in said plenum chamber; and
    an outflow from said plenum chamber.

2. The system of claim 1, wherein said pulse attenuator is an attenuation chamber and an orifice arranged such that fluid pumped by the pump is in communication with the attenuation chamber before flowing through the orifice.

3. The system of claim 2, wherein said pulse attenuator includes two orifices along a fluid pathway from said pump to the plenum chamber.

4. The system of claim 1, wherein said volume sensor is a float sensor.

5. The system of claim 1 further including an intake filter positioned between said pump and said pulse attenuator such that pumped fluid liquid moves through said filter.

6. The system of claim 5, wherein said intake filter is a 0.2 micron filter.

7. The system of claim 1 further comprising an air flow filter filtering air from said pressurization source.

8. The system of claim 1 wherein said pressurization source includes a pressure regulator.

9. A system for delivery of constant flow liquid from a supply container, the system comprising:
    a fluid pump pumping fluid from the supply container;
    an attenuation chamber coupled by tubing to the pump;
    an orifice coupled by tubing to the pump such that fluid communicates with the attenuation chamber before passing through the orifice;
    a plenum chamber in fluid communication with said orifice such that pulse attenuated flow enters into said chamber;
    a volume sensor that senses fluid level within said plenum chamber and activates the pump to keep fluid level within the plenum chamber within a defined range;
    a pressurization source in fluid communication with said plenum chamber, said source providing a pressure head in said plenum chamber; and
    a plenum chamber outlet.

10. The system of claim 9, further comprising a second orifice along a fluid pathway from said pump to the attenuation chamber.

11. The system of claim 9, wherein said volume sensor is a float sensor.

12. The system of claim 9 further including an intake filter positioned between said pump and said pulse attenuator such that pumped fluid moves through said filter.

13. The system of claim 12, wherein said intake filter is a 0.2 micron filter.

14. The system of claim 9 further comprising an air flow filter filtering air from said pressurization source.

15. The system of claim 9 wherein said pressurization source includes a pressure transducer.

16. In a system for providing pulse free sheath flow fluid to a flow cytometer, said system including a pump, which withdraws fluid from a vented container and transfers fluid to a holding chamber along a fluid pathway, said holding chamber having a regulated pressure and having an outflow to a flow cytometer, an improvement wherein interposed between said pump and said holding chamber is a fluid pulse attenuator comprising an attenuation chamber and an orifice, wherein said fluid pathway gasses through said attenuation chamber and said orifice in series.

17. The system of claim 16, further comprising a second orifice along said fluid pathway positioned between said pump and said attenuation chamber.

18. The system of claim 16 further including an intake filter positioned between said pump and said pulse attenuator such that pumped fluid moves through said filter.

19. The system of claim 18, wherein said intake filter is a 0.2 micron filter.

20. The system of claim 16 further comprising a pressurization source and an air flow filter filtering air from said pressurization source.

21. The system of claim 16 wherein said pressurization source includes a pressure transducer.

* * * * *